United States Patent [19]

Heiba et al.

[11] 4,328,363

[45] * May 4, 1982

[54] MANUFACTURE OF GAMMA HALOGEN SUBSTITUTED ADDUCTS

[75] Inventors: El-Ahmadi I. Heiba, Princeton; Ralph M. Dessau, Edison, both of N.J.

[73] Assignee: Mobil Oil Corporation, New York, N.Y.

[ * ] Notice: The portion of the term of this patent subsequent to Mar. 8, 1994, has been disclaimed.

[21] Appl. No.: 958,756

[22] Filed: Nov. 8, 1978

Related U.S. Application Data

[63] Continuation-in-part of Ser. No. 775,145, Mar. 7, 1977, abandoned, which is a continuation-in-part of Ser. No. 400,484, Sep. 24, 1973, Pat. No. 4,011,239, which is a continuation-in-part of Ser. No. 755,732, Aug. 27, 1968, abandoned, which is a continuation-in-part of Ser. No. 714,447, Mar. 20, 1968, abandoned.

[51] Int. Cl.$^3$ .................. C07C 67/00; C07C 45/69
[52] U.S. Cl. ................... 560/82; 260/465 C; 260/465 D; 260/465.3; 560/192; 560/204; 568/316; 568/317; 568/393; 568/433; 568/458
[58] Field of Search ............ 560/82, 192; 260/590 E, 260/597, 465 C, 465 D, 465.3; 568/316, 317, 393, 433, 458

[56] References Cited

U.S. PATENT DOCUMENTS

| | | | |
|---|---|---|---|
| 3,123,629 | 3/1964 | Julia | 560/124 |
| 3,354,196 | 11/1967 | Julia | 560/124 |
| 4,011,239 | 3/1977 | Heiba et al. | 560/176 |

FOREIGN PATENT DOCUMENTS 1269119 4/1972 United Kingdom .

OTHER PUBLICATIONS

Elliott, Bulletin of World Health Organization, 44, No. 1-3, pp. 315-323, (1970).
March, *Advanced Organic Chemistry*, pp. 287-290, (1965).

Primary Examiner—Natalie Trousof
Assistant Examiner—Vera C. Clarke
Attorney, Agent, or Firm—Charles A. Huggett; Michael G. Gilman; Larry B. Hobbes

[57] ABSTRACT

Halogen-substituted olefin addition compounds that contain a carbonyl group are formed by oxidatively adducting an olefin and a carbonyl compound such as a ketone, aldehyde, or ester. The method consists of reacting the olefin and the carbonyl component, in solution, with an oxidizing ion of manganese, cerium or vanadium in the presence of fluoride, chloride or bromide ion. This ionic component is incorporated in the adduct and appears on the olefin-derived carbon atom gamma to the carbonyl group. The gamma halogen substituted adducts are readily converted to cyclopropane derivatives, including pyrethroid intermediate compounds.

15 Claims, No Drawings

MANUFACTURE OF GAMMA HALOGEN SUBSTITUTED ADDUCTS

CROSS REFERENCE TO RELATED APPLICATIONS

This application is a continuation-in-part of application Ser. No. 775,145 filed Mar. 7, 1977, now abandoned, which, in turn, is a continuation-in-part of Ser. No. 400,484, Sept. 24, 1975, now U.S. Pat. No. 4,011,239 issued Mar. 8, 1977, which in turn was a continuation-in-part of copending Application Ser. No. 755,732, filed Aug. 27, 1968, now abandoned. This latter application was a continuation-in-part of copending application Ser. No. 714,447 filed Mar. 20, 1968, now abandoned.

BACKGROUND OF THE INVENTION

1. Field of the Invention

This invention relates to a method for the preparation of a halogen-substituted organic compound by the reaction of an olefin with an organic carbonyl compound which may contain certain other functional groups described hereinbelow. In particular, it relates to the preparation of an oxidatively coupled adduct of an olefin in which an atom of halogen is incorporated into the molecular structure during the reaction.

2. Description of Background Synthesis

U.S. Pat. No. 4,011,239 issued Mar. 8, 1977, of which the present invention is a continuation-in-part, describes a method for oxidatively adducting an olefin with a ketone, an aldehyde, an ester, a nitrile, a nitroparaffin, a sulfoxide, a thiosulfonic acid ester, an alkanesulfonic acid, an alkanesulfinic acid, or a thiol. The reaction whereby the olefin and other component is oxidatively adducted is effected by reacting the two organic components in solution in the presence of a stoichiometric amount of an ion of manganese, cerium, or vanadium in a valence state higher than the lower valence state above the zero valent form of the metal. During the reaction, the ion of manganese, cerium or vanadium, which must be an oxidizing ion in the reaction environment, is reduced to a lower valent form as shown hereinbelow.

In the above-identified U.S. Pat. No. 4,011,239, the adduction reaction is described as proceeding via the free radical .X formed in the reaction between the ketone, aldehyde, etc. and the oxiding ion. The free radical .X in turn reacts with the compound having olefinic unsaturation, i.e. the olefin. The .X radical reacted with the compound have olefinic unsaturation is one selected from the following classes:

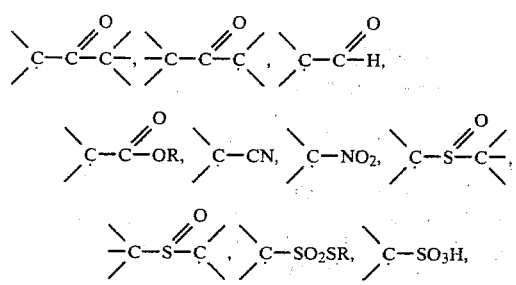

These free radicals are derived respectively from a symmetrical or an unsymmetrical ketone, an aldehyde, an ester, a nitrile, a nitroparaffin, a symmetrical or unsymmetrical sulfoxide, a thiosulfonic acid ester, an alkanesulfonic acid, an alkanesulfinic acid, and a thiol.

In the free radicals described above, the dangling valences may be satisfied by a wide variety of groups. R is generally an alkyl group. R' is generally a hydrocarbyl or substituted hydrocarbyl group. The method is capable of providing high yields of valuable products containing the moiety

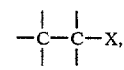

where X is one of the radicals just defined.

As a specific example, the reaction sequences and the types of products obtained with the ketone-derived radical

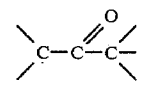

are described in the forementioned patent. The sequences are herein repeated in equation form (Equations 1-5), with the olefin designated as R"CH=CH$_2$, R" being hydrogen or a hydrocarbyl group. Further, Mn+++ is used as the metal ion, and manganic acetate as the source of the Mn+++,

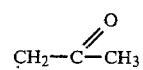

as the specific free radical, and acetone as the ketone from which the specific free radical is derived. As shown in equation (I), the

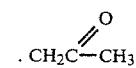

free radical is produced when manganic acetate, dissolved in acetic acid, is heated with acetone. According to the reaction of equation (2), the reactive acetylmethyl free radical,

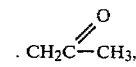

adds to the double bond of the olefin, forming the free radical (A). In equation (3), oxidation of free radical intermediate (A) occurs in the presence of manganic acetate to form the cation intermediate (B), with reduction of Mn$^{+3}$ to Mn$^{+2}$ and formation of an acetate ion. In equation (4), the cation (B) reacts with the acetate ion to form the keto-ester product (P-1), about 90% of the $Mn^{+3}$ consumed forming this product. As shown in equation (5), about 10% of the $Mn^{+3}$ consumed forms the beta-gamma unsaturated ketone product (P-2) by losing H. If R" is hydrogen, the product (P-1) is 1-acetoxy-pentanone-4, and (P-2) is 1-penten-4-one. It is pointed out that the acetylmethyl free radical is not substantially oxidized by $Mn^{+3}$, but the free radical intermediate (A) is readily oxidized, thus providing a case of selective oxidation. In other words, (A) has a lower ionization potential than the acetylmethyl radical. The ion intermediate (B) may react in either of two ways, as shown in equations (4) and (5).

As disclosed in U.S. Pat. No. 4,011,239, certain circumstances may induce products other than (P-1) and (P-2) to form. For example, when R" is a phenyl group, the unsaturated ketone product (P-2) is not obtained; rather, a dihydrofuran product forms instead. Also, when the solvent contains water, thus providing hydroxyl ion, some of the product (P-1) contains a simple hydroxyl substituent in place of the acetate ester group shown.

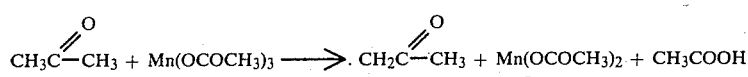

Equation (1)

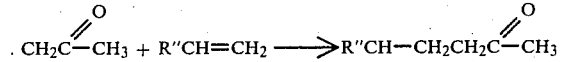

Equation (2)

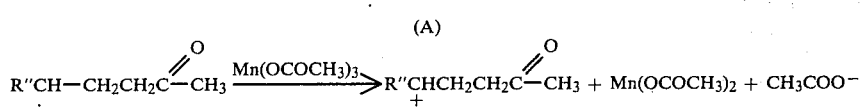

Equation (3)

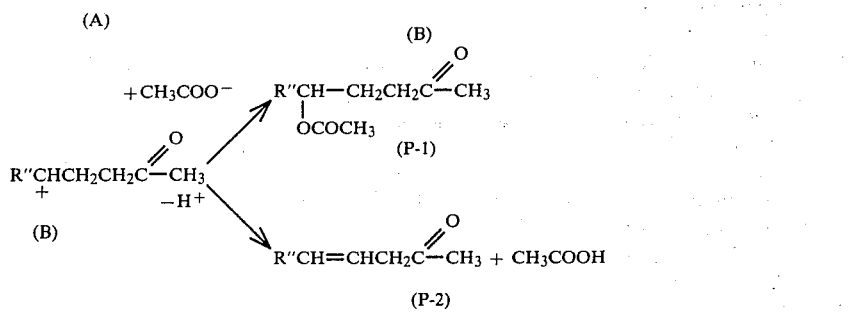

Equation (4)

Equation (5)

It is clear from the foregoing description that the overall reaction requires two equivalents of oxidizing ion per mole of product that is formed, i.e. a stoichiometric amount of oxidizing ion of manganese, cerium or vanadium. Actually, in practice, some of the oxidizing ion may be consumed in side reactions, so that somewhat more than the required two equivalents are consumed overall per mole of product. The reaction thus is clearly distinguished from those reactions in which a catalytic amount of metal ion is used.

Another aspect of the adduction reaction is that the functional group of the compound that forms the radical .X is preserved in the adducted product. Thus, reacting an olefin with a ketone forms an adduct which itself is a ketone; with an aldehyde as reactant, an adduct is formed which itself is an aldehyde; and with a diester, an adduct which also is a diester.

The entire contents of U.S. Pat. No. 4,011,239, which describes the background synthesis involved in the present invention, is incorporated herein by reference.

BRIEF SUMMARY OF THE INVENTION

It has now been discovered that when the adducting reaction described above is conducted in the presence of a soluble fluoride, chloride or bromide salt, thus providing a source of halogen ion, the adduct formed contains a halogen substituent on the olefin-derived carbon atom gamma to the functional group. Thus, a method is described for preparing a halogen substituted adduct of an olefin and an adductable organic compound selected from the group consisting of a ketone, aldehyde, ester, nitrile, nitroparaffin, sulfoxide, thiosolfonic acid ester, alkanesulfonic acid, alkanesulfinic acid and thiol. Briefly, the method comprises reacting, in solution, and olefin, the adductable organic compound, and a stoichiometric amount of an oxidizing ion of manganese, cerium or vanadium, said reaction being conducted in the presence of fluoride, chloride or bromide ion. In a preferred embodiment of this invention, the adductable organic compound is an organic carbonyl compound such as a ketone, an aldehyde or an ester.

While not wishing to be bound by theory, it is believed that the halogen-substituted adduct is formed by a reaction path similar to that shown above in equations (1) to (5) for the background synthesis; however, the halide ion, such as chloride, is added instead of the acetate ion shown in equation (4), to give the gamma chloro-substituted adduct

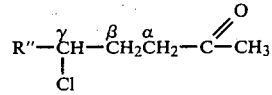

along with the olefinic adduct (P-2) shown in equation (5). Other modifications of reaction path could conceivably be proposed, but in all cases two equivalents of the oxidizing ion are required per mole of adduct which is formed.

In another aspect of this invention, it is contemplated to convert the gamma halogen substituted adduct to cyclopropane derivatives by known methods, thereby providing an improved synthesis of pyrethroid compounds of the cyclopropane-derivative variety.

DETAILED DESCRIPTION OF THE INVENTION

In general, any organic compound that contains at least one ethylenically unsaturated double bond may be used as the olefin in the present invention. The olefin also may be defined as

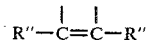

with both of R" being equal to hydrogen, a hydrocarbyl group, or an organyl group, and with one R" being the same as or different from the other R". The term "hydrocarbyl" designates any group containing only carbon and hydrogen, such as alkyl, alkenyl, alkynyl, aryl, alkaryl, aralkyl, etc., and the term "organyl" designates hydrocarbyl and substituted hydrocarbyl, including heterocyclic, groups. Suitable illustrative olefins include ethylene, propylene, the butenes, pentenes, hexenes, heptenes, octenes, nonenes, decenes, undecenes, dodecenes, tetradecenes, pentadecenes, hexadecenes, octadecenes, eicosenes, hexacosenes, triacontenes, etc. These may be straight or branched chain olefins with the double bond in the 1-position or any other position. Olefin oligomers are useful, such as propylene tetramer, isobutylene trimer, propylene pentamer, isobutylene tetramer, propylene hexamer, etc. Also suitable are open chain, conjugated or unconjugated diolefins having 3 to 20 or 30 or more carbons, and including allene, butadiene, isoprene, pentadiene, hexadiene, heptadiene, diisobutenyl, decadiene, and the like; also substituted diolefins like 2-cyanobutadiene, and chloroprene. Also of use are open chain olefins having more than two double bonds, sometimes designated oligo-olefins, such as hexatriene, 2,6-dimethyl-2,4,6-octatriene, etc. Cyclic olefins are suitable, such as cyclopentene, cyclohexene, cycloheptene, cyclooctene, and terpenes such as the various menthenes, thujenes, carenes, pinenes, and bornylenes; also cyclic diolefins and cyclic oligo-olefins like cyclobutadiene, cyclopentadiene, fulvene, norbornadiene, cyclooctadiene, 4-vinylcyclohexene, limonene, dipentene, dicyclopentadiene, cycloheptatriene, cyclooctatriene, bicyclo(2.2.2)oct-2,5.7-triene, cyclonona-1,4,7-triene, cyclooctatetraene, and the like. Olefins having both double and tripel bonds are of value, such as butenyne, 1,6-heptadiene-3-yne, 3,6-dimethyl-2,6-octadiene-4-yne, 1,7-octaenyne, etc. Vinyl chloride, styrene and vinyl naphthalene may be used.

It will be seen that nearly all of the foregoing compounds are hydrocarbons having one, two or more double bonds and having an open chain or a cyclic structure. Particularly effective are terminal olefins. It will be apparent that many of the foregoing R" groups are hydrocarbyl groups. The dangling valences in the expression,

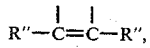

may be satisfied by any suitable groups, such as hydrogen, alkyl, alkenyl, aryl, or any of the groups noted above represented by R". For the purposes of this invention, olefins may contain from 2 to about 80 carbon atoms.

When it is desired to use this invention to prepare pyrethroid compounds, the particularly useful olefins are those having from 2 (two) to about 12 (twelve) carbon atoms, and many of these are characterized by the presence of an organyl group, R", which contains one or two chlorine or bromine atoms. Bromine- and chlorine-substituted butadienes are particularly useful. Illustrative of such olefins having from 2 to 12 carbon atoms are the following:

1,1-dichloro-4-methylbutadiene
1,1-dichloro-4,4-dimethylbutadiene
1,1-dibromo-4-methylbutadiene
1,1-dibromo-4,4-dimethylbutadiene
1-carbomethoxy-1-methyl-4-methylbutadiene
1-carbomethoxy-1-methyl-4,4-dimethylbutadiene
1-carboethoxy-1-methyl-4-methylbutadiene
1-carboethoxy-1-methyl-4,4-dimethylbutadiene
1,1-dibromoethylene
1,1-dichloroethylene
3-hydroxy-3-methylbutene-1
vinylcyclohexane
1-hydroxy-1-vinylcyclohexane
vinylcyclopentane
1-hydroxy-1-vinylcyclopentane A large number of adductable compounds exist which are useful in the present invention. Of course, in order to form the radical intermediate, there must be at least one hydrogen on the carbon atom adjoining the functional group, which is the carbonyl group in the preferred ketone, aldehyde ester or nitrile reactant.

The preferred class of adductable organic compounds is that which contains a carbonyl group within its structure. This class thus includes the symmetrical and unsymmetrical ketones, the aldehydes, and esters. Nitrile compounds, especially malononitrile, are also very effective. Compounds which contain more than one carbonyl group also may be used. Specific ketones useful in this invention include acetone, acetoacetic ester, methylethyl ketone, diethyl ketone, methylpropyl ketone, methylisopropyl ketone, acetophenone, and cyclohexanone. In the present invention, an unsymmetrical ketone will form a radical intermediate by preferential abstraction of a hydrogen on the least highly substituted carbon atom alpha to the carbonyl, but some of the more highly substituted carbon atom will also form radicals. Thus, both adducts will form but the adduct with the least substituted carbon will predominate.

Aldehydes which are useful in this invention include ethanal, propanal, butanal, buten-2-al, pentanal, pentenal, hendecanal, and other straight or branched chain aliphatic aldehydes having any desired number of carbons. An aromatic aldehyde like benzaldehyde or naphthaldeyde is excluded because it contains no abstractable hydrogen on the carbon atom alpha to the carbonyl group, but aldehydes like phenyl acetaldehyde, phenylpropionaldehyde, 2-pyridinepropionaldehyde, etc. are of use.

Esters which are useful in this invention include cyanoacetic ester, methyl acetate, methyl propionate, ethyl butyrate, and other aliphatic esters having any suitable number of carbons. Aromatic esters having at least one hydrogen atom on the carbon alpha to the carbonyl group are useful, such as alkyl esters of phenylacetic, phenylpropionic, coumaric, and other acids. Diesters such as malonic ester can also be employed.

It is to be understood, of course, that for purposes of this invention the organic carbonyl compound may have more than one carbonyl group, or substituents in addition to the carbonyl group such as cyano, fluoro, chloro, bromo, hydroxyl, thiol, etc., and may additionally contain unsaturated olefinic or acetylenic bonds.

The preferred oxidizing metal ion for oxidatively coupling the olefin and the adductable organic compound is trivalent manganese, or manganic ion $Mn^{+3}$, which, as indicated above, is reducible during the reaction to bivalent manganese, or manganous ion $Mn^{+2}$. As shown above by equations (1)–(5), the $Mn^{+3}$, and the manganic acetate which provides it, are reactants. Manganic acetate dihydrate is a preferred $Mn^{+3}$-producing compound; it may be formed by oxidizing an acetic acid solution of manganous acetate with potassium permanganate. Other suitable $Mn^{+3}$-producing source compounds or mixtures include anhydrous manganic acetate; also a mixture of activated (i.e., freshly prepared or acid treated) manganese dioxide and acetic acid; a mixture of manganese sesquioxide and acetic acid; and a mixture of $Mn_3O_4$ and acetic acid. Also a solution of manganese chloride and acetic acid; or manganese fluoride, or manganic hypophosphate dihydrate, or manganic sulfate, or manganic phosphate monohydrate, or manganic pyrophosphate, or manganic propionate, each dissolved in acetic acid or one of the solvents noted below. Other higher-valent manganese ions, in solution, may be of use, such as $Mn^{+4}$, as obtained from a mixture of $MnO_2$ and acetic acid; also $Mn^{+6}$, as supplied by the manganate of sodium, potassium, ammonium, lithium, magnesium, strontium, calcium or barium, etc.; also $Mn^{+7}$, as supplied by the permanganate of sodium, ammonium, potassium, or magnesium, etc. Whatever higher-valent manganese ion-supplying compound is chosen, it should be soluble in the solvent as described below. In addition to the foregoing higher-valent manganese ions, it is feasible to employ mixtures of ions, such as $Mn^{+2}$ plus any of $Mn^{+3}$, $Mn^{+4}$, $Mn^{+6}$, or $Mn^{+7}$; or $Mn^{+3}$ plus any of $Mn^{+4}$, $Mn^{+6}$, or $Mn^{+7}$; or $Mn^{+4}$ plus $Mn^{+6}$ or $Mn^{+7}$; or $Mn^{+6}$ plus $Mn^{+7}$. Such mixtures may be supplied by suitable mixtures of the foregoing source compounds. The $Mn^{+2}$ ion may be supplied by any soluble manganous compound, such as the acetate, propionate, nitrate, oxide, hydroxide, chloride, sulfate, phosphate, perchlorate, etc.

The manganese source compound may be added per se to the reaction mixture, or if desired it may be formed in situ. In situ formation may suitably be performed by adding to the reaction mixture a manganous compound like manganous acetate together with a solvent therefor like acetic acid and also adding an oxidizing agent so that the $Mn^{+2}$ ion is oxidized at least to $Mn^{+3}$ ion. Other manganous compounds include those named in the preceding paragraph, and other solvents include alkali metal acetates and carbonates as well as those described below. Suitable oxidizing agents include nitric acid, potassium permanganate, chlorine, oxygen, air, potassium manganate, cerium ammonium nitrate, cobaltic acetate, various peroxides like peracetic acid and hydrogen peroxide, or intermediates peroxides or hydroperoxides resulting from the air oxidation of hydrocarbons. Electrochemical oxidation is a suitable oxidizing procedure.

Besides manganese, cerium and vanadium also are of use in the reaction. Each of these metal ions has at least two valency states, a lower and a higher, above the zero valent form of the metal. Thus, manganese has valency states of 2, 3, 4, 6, and 7, cerium has valency states of 3 and 4, and vanadium has valency states of 2, 3, 4, and 5. Each is available, in a higher-valent state, as the acetate, or other suitable compound, which is decomposable under the conditions of the reaction to give a metal ion of lower valence. In their higher valency states, these metal ions have a relatively good oxidation potential, and in their lower valency states, they tend to be stable and reoxidizable to the higher valency states.

The reaction between the olefin and adductable organic compound is conducted in a solvent for the oxidizing ion employed. As a solvent, glacial acetic acid is preferred. However, other fatty acids such as propionic and butyric acids also may be used. In some instances, the enolizable compound itself may be used as solvent, and should be used preferably in excess to facilitate dissolution of the oxidizing ion and the compound providing the halide ion.

For the purposes of this invention, a soluble fluoride, chloride, or bromide salt is included in the reaction mixture during formation of the adduct. Salts which may be used include ammonium and the alkali metal salts hydrofluoric acid, hydrochloric acid or hydrobromic acid. Lithium flouride, lithium chloride and lithium bromide are particularly preferred because of high solubility. Alternatively, anhydrous or aqueous hydrogen fluoride, hydrogen chloride, or hydrogen bromide may be used to provide the desired fluoride, chloride or bromide ion in the reactant solution.

It will be clear from the foregoing description and the examples which follow that the reaction of this invention proceeds in stoichiometric fashion to form the olefin adduct, i.e. one mol of adduct requires the reaction of one mol of olefin, one mol of adductable organic compound and one mol of halide ion, with two equivalents of oxidizing ion being consumed in the reaction. In the conduct of the reaction, the concentration of the olefin may range from 0.01 to 5 moles or more of olefin per mol of manganic or other higher-valent oxidizing ion. In general, it is preferred that the olefin be present in stoichiometric concentration with respect to the manganic ion, or in excess when this is found to facilitate the reaction. Likewise, the adductable organic compound and the source of halide ion should be present in at least about stoichiometric concentration with regard to the oxidizing ion; the judicious use of excess concentrations, depending on the choice of reactants and reaction conditions, may lead to improved yields of the desired adduct. When excess concentrations are used, the reaction still proceeds in stoichiometric fashion and the unreacted excess may be recovered and recycled. The solvent, such as acetic acid, should be present in an amount sufficient to dissolve the olefin and the metal compounds. The reaction is suitably performed by refluxing the foregoing components, although lower temperatures may be used, ranging from about 40° to 100° C. Temperatures above boiling are of use but in this case the reaction is performed under pressure to maintain a liquid phase. Reaction times generally extend from an hour or less to 5 or 10 hours or more. An inert atmosphere, such as one of nitrogen, carbon dioxide, helium, and the like is desirably maintained over the reaction mixture to lessen or avoid oxidation by air.

At the conclusion of the reaction, separation of the product may be effected as by conventional distillation, extraction, fractional crystallization, and the like with or without the aid of conventional filtration or centrifugation. It will be recognized that the reduced form of the oxidizing ion of manganese, cerium or vanadium may be recovered, reoxidized and reused.

Although not required for the purposes of this invention, the reaction in some cases is found to proceed more readily when a trace amount of copper salt, such as cupric chloride, is present. A concentration of $10^{-3}$ to $10^{-5}$ of cupric chloride, or of ferric chloride, for example, is effective as adjuvant.

The halogen substituted adducts prepared by the method of this invention can be readily converted to substituted cyclopropanes by treatment with potassium t-butoxide, for example, thus forming pyrethroid compounds.

An olefin particularly suited for the preparation of a pyrethroid intermediate compound according to this invention is selected from the group consisting of 1,1-dichloro-4-methylbutadiene, 1,1-dichloro-4,4-dimethylbutadiene, 1,1-dibromo-4-methylbutadiene, 1,1-dibromo-4,4-dimethylbutadiene, 1-carbomethoxy-1-methyl-4-methylbutadiene, 1-carbomethoxy-1-methyl-4,4-dimethylbutadiene, 1-carboethoxy-1-methyl-4-methylbutadiene, 1-carboethoxy-1-methyl-4,4-dimethylbutadiene, 1,1-dibromoethylene, 1,1-dichloroethylene, 3-hydroxy-3-methylbutene-1, vinylcyclohexane, 1-hydroxy-1-vinylcyclohexane, vinylcyclopentane, and 1-hydroxy-1-vinylcyclopentane.

In general, the gamma-halogen substituted adducts formed by the method of this invention have various utilities. They may be used as intermediates in chemical synthesis, for example, to form intermediate pyrethroid compounds with insecticidal activity. The pyrethroid compounds of the substituted cyclopropane variety are formed, for example, by elimination of HCl from the gamma-halogen substituted adduct according to the general reaction, wherein R″ is as above-defined and the dangling valences represent R″ or halogen:

$$-\underset{\underset{Cl}{|}}{\overset{|}{C^\gamma}}-\underset{|}{\overset{|}{C^\beta}}-\underset{\underset{H}{|}}{\overset{|}{C^\alpha}}-\overset{O}{\overset{\|}{C}}-R'' \xrightarrow[\text{base}]{-HCl} -\underset{|}{\overset{|}{C^\beta}}\underset{\diagdown\ \diagup}{\phantom{xx}}\underset{|}{\overset{|}{C^\alpha}}-\overset{O}{\overset{\|}{C}}-R''$$
$$\phantom{xxxxxxxxxxxxxxxxxxxxxxxxxxx}\diagup C^\gamma \diagdown$$

Bases such as sodium methoxide, sodium tert-butoxide, pyridine, alcoholic KOH and others are effective in inducing formation of the substituted cyclopropane.

With reference to other utilities for the halogen substituted adducts of this invention, detergents useful in lubricating oils may be formed by adducting olefins having at least about eight carbon atoms with ethers. Or, organic solvents and plasticizers may be formed by adducting olefins having two carbon atoms or more with organic carbonyl compounds.

The following examples are merely illustrative of the invention and are not to be construed as limiting thereon. All parts and percentages given are by weight unless specifically stated to be on a different basis.

EXAMPLE 1

Preparation of Manganic Acetate Solution

A solution of 73 g Mn(OAc)$_2$.2H$_2$O in 700 ml acetic acid was heated to 65° C., and 12.6 g KMnO$_4$ was added. The resulting solution was heated to 95° C. and 33 ml acetic anhydride was added. This solution was then used in the following reactions:

EXAMPLE 2

The solution of Example 1 was added to a solution containing 50 ml styrene, ($\phi$—CH=CH$_2$), 183 ml dimethyl malonate, and 42 g LiCl in 400 ml acetic acid maintained at 55° C. under N$_2$. The brown manganic color disappeared within 15 minutes and the reaction mixture was worked up by extraction with hexane and water. The hexane extract was dried and the solvent stripped under reduced pressure. The crude product was distilled and the fraction boiling at 125°–130° C./0.08 mm Hg was collected. This product which was obtained in 27% yield based on manganic ion was identified as $$\phi\text{-CHCH}_2\text{CH(COOCH}_3)_2$$
$$\phantom{xx}|$$
$$\phantom{xx}\text{Cl}$$

by spectral means.

EXAMPLE 3

A solution of manganic acetate was prepared by reacting:
  275 g Mn(OAc)$_2$.2H$_2$O
  1400 ml acetic acid
  55 g KMnO$_4$
  120 ml acetic anhydride
To this solution, at 60° C., was added
  200 g LiCl followed by
  250 ml octene-1 and
  500 ml acetone
After 45 minutes, the brown manganic color had disappeared and the reaction mixture was worked-up in the usual manner. The product was isolated by distillation at 100°–115° C./0.08 mm Hg in 30% yield based on permanganate used. The product was identified as 5-chloro-undecanon-2

$$(\text{C}_6\text{H}_{13}-\text{CHCH}_2\text{CH}_2-\overset{\text{O}}{\overset{\|}{\text{C}}}\text{CH}_3)$$
$$\phantom{xxxxxx}|$$
$$\phantom{xxxxxx}\text{Cl}$$

by spectral means.

EXAMPLE 4

To a solution of 73 g Mn(OAc)$_2$.2H$_2$O in 700 ml acetic acid was added 12.6 g KMnO$_4$ at 95° C. After 1 hour, 70 g lithium acetate dihydrate was added. This solution was then added to a second solution containing 600 ml acetone, 35 ml styrene, ($\phi$—CH=CH$_2$), 200 ml acetic acid, 60 g LiOAc.2H$_2$O and 16.9 g LiCl at 45°–60° C. The reaction was over in one-half hour and the product was isolated by extraction and distillation (bp ~75°/0.1 mm Hg). The product was identified as $$\phi\text{-CHCH}_2\text{CH}_2-\overset{\text{O}}{\overset{\|}{\text{C}}}\text{CH}_3$$
$$\phantom{xx}|$$
$$\phantom{xx}\text{Cl}$$

by spectral means.

EXAMPLE 5

Conversion of the γ-chlorocarbonyl compound to cyclopropyl derivative was accomplished by treating the above product (0.5 g) dissolved in diethyl ether with 0.5 g potassium t-butoxide. 1-phenyl-2-acetyl cyclopropane was formed in excellent yield.

EXAMPLE 6

To a solution of 47 ml octene-1, 75 ml acetylacetone, and 21.2 g LiCl in 500 ml acetic acid was added 42.7 g Mn(OAc)₃.2H₂O. The reaction mixture was heated at 60° C. under N₂ until the brown manganic color had disappeared.

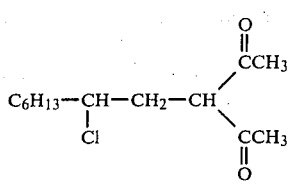

was formed in 60% yield based on manganic acetate used.

What is claimed is:

1. A method for manufacturing a halogen-substituted pyrethroid intermediate compound which comprises: reacting in acetic solution:

an olefin having the structure

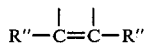

wherein each R″ is hydrogen or an organyl group,
an adductable organic compound selected from the group consisting of a ketone, an aldehyde, an ester, a nitrile, a nitroparaffin, a sulfoxide, a thiosulfonic acid ester, an alkanesulfonic acid, an alkanesulfinic acid, and a thiol, said adductable compound having two abstractable hydrogen atoms on a carbon atom alpha to said group,
and a stoichiometric amount of an oxidizing ion of manganese, said reaction being conducted in the presence of fluoride, chloride or bromide ion;
and recovering the fluorine-, chlorine-, or bromine-substituted adduct of said olefin.

2. The method of manufacture described in claim 1 wherein said adductable organic compound is an organic carbonyl compound and said ion of manganese is trivalent manganic ion.

3. The method of manufacture described in claim 2 wherein said organic carbonyl compound is an ester.

4. The method of claim 3 wherein said ester is dimethylmalonate.

5. The method of manufacture described in claim 2 wherein said organic carbonyl compound is an aldehyde.

6. The method of manufacture described in claim 2 wherein said organic carbonyl compound is a ketone.

7. The method of manufacture described in claim 6 wherein said ketone is acetone.

8. The method of manufacture described in claim 6 wherein said ketone is acetylacetone.

9. The method described in claim 1 wherein said reaction is conducted in the presence of chloride ion and said recovered adduct is chlorine-substituted.

10. The method described in claim 2 wherein said reaction is conducted in the presence of chloride ion and said recovered adduct is chlorine-substituted.

11. The method described in claim 2 wherein said olefin contains from 2 (two) to about 12 (twelve) carbon atoms.

12. The method described in claim 2 wherein there is also present during said reaction a concentration of $10^{-3}$ to $10^{-5}$ mols/liter cupric chloride or ferric chloride.

13. The method of manufacture described in claim 1 wherein said adductable organic compound is selected from the group consisting of dialkylmalonate, a malononitrile, a β-ketoester, a cyanoacetic ester, a cyanoacetic acid and a β-dicarbonyl compound; and said olefin contains as additional functional group a double bond, a halogen, or a hydroxyl group.

14. The method described in claim 11 wherein the olefin is a diene and contains at least one halogen substituent or hydroxyl group substituent.

15. The method described in claim 14 wherein the olefin is selected from the group consisting of 1,1-dichloro-4-methylbutadiene, 1,1-dichloro-4,4-dimethylbutadiene, 1,1-dibromo-4-methylbutadiene, 1,1-dibromo-4,4-dimethylbutadiene, 1-carbomethoxy-1-methyl-4-methylbutadiene, 1-carbomethoxy-1-methyl-4,4-dimethylbutadiene, 1-carboethoxy-1-methyl-4-methylbutadiene, 1-carboethoxy-1-methyl-4,4-dimethylbutadiene, 1,1-dibromoethylene, 1,1-dichloroethylene, 3-hydroxy-3-methylbutene-1, vinylcyclohexane, 1-hydroxy-1-vinylcyclohexane, vinylcyclopentane, and 1-hydroxy-1-vinylcyclopentane.

* * * * *